United States Patent
Perez-Bolivar et al.

(10) Patent No.: US 10,458,627 B2
(45) Date of Patent: Oct. 29, 2019

(54) THIN FILM SHEET INCLUDING POWER LINES, LIGHTS, AND SENSORS

(71) Applicant: Grote Industries, LLC, Madison, IN (US)

(72) Inventors: Cesar Perez-Bolivar, Madison, IN (US); Michael R. Henderson, Madison, IN (US); Adam Slade, Madison, IN (US); Jiabiao Ruan, Madison, IN (US); Charles D. Polley, Madison, IN (US)

(73) Assignee: Grote Industries, LLC, Madison, IN (US)

( * ) Notice: Subject to any disclaimer, the term of this patent is extended or adjusted under 35 U.S.C. 154(b) by 0 days.

(21) Appl. No.: 15/724,613

(22) Filed: Oct. 4, 2017

(65) Prior Publication Data

US 2018/0100640 A1 Apr. 12, 2018

Related U.S. Application Data

(60) Provisional application No. 62/405,431, filed on Oct. 7, 2016.

(51) Int. Cl.
| | |
|---|---|
| *F21V 19/00* | (2006.01) |
| *B60Q 3/70* | (2017.01) |
| *F21V 23/06* | (2006.01) |
| *G01K 1/14* | (2006.01) |
| *B60Q 3/30* | (2017.01) |
| *F21V 3/02* | (2006.01) |
| *G01N 33/00* | (2006.01) |
| *H01B 7/00* | (2006.01) |

(52) U.S. Cl.
CPC ............ *F21V 19/0065* (2013.01); *B60Q 3/30* (2017.02); *B60Q 3/70* (2017.02); *F21V 23/06* (2013.01); *G01K 1/14* (2013.01); *F21V 3/02* (2013.01); *G01N 33/0047* (2013.01); *H01B 7/0045* (2013.01)

(58) Field of Classification Search
None
See application file for complete search history.

(56) References Cited

U.S. PATENT DOCUMENTS

| | | | |
|---|---|---|---|
| 7,128,442 B2 | 10/2006 | Lee et al. | |
| 8,814,415 B2 | 8/2014 | Kim et al. | |
| 9,087,973 B1* | 7/2015 | Perez-Bolivar | H01L 33/62 |
| 9,214,615 B2* | 12/2015 | Tischler | H01L 21/78 |
| 2005/0212406 A1* | 9/2005 | Daniels | F21K 9/90 |
| | | | 313/503 |

(Continued)

OTHER PUBLICATIONS

International Search Report and Written Opinion of the International Searching Authority dated Dec. 11, 2017 in connection with the corresponding PCT international patent application No. PCT/US2017/055099.

*Primary Examiner* — Elmito Breval
(74) *Attorney, Agent, or Firm* — Posz Law Group, PLC (57) ABSTRACT

A thin film sheet that includes a substrate, a first electrical connector, a second electrical connector, and one or more light sources and sensors electrically connected to the first and second electrical connectors within the thin film sheet. The first and second electrical connectors attach to the substrate and transmit power and/or information to and from the light sources and sensors, and the second electrical connector extends parallel to the first electrical connector.

10 Claims, 5 Drawing Sheets

(56) References Cited

U.S. PATENT DOCUMENTS

| | | |
|---|---|---|
| 2008/0211413 A1 | 9/2008 | Nakamura et al. |
| 2012/0162984 A1* | 6/2012 | Fujimori ............... H01L 33/360 |
| | | 362/235 |
| 2014/0062315 A1* | 3/2014 | Tischler ............. H05B 33/0827 |
| | | 315/185 R |
| 2014/0062316 A1* | 3/2014 | Tischler ............. H05B 33/0821 |
| | | 315/185 R |
| 2014/0362566 A1 | 12/2014 | Tischler et al. |
| 2015/0371972 A1* | 12/2015 | Jones ................ H01L 25/0753 |
| | | 257/89 |
| 2015/0380390 A1* | 12/2015 | Weekamp ............... H01L 33/62 |
| | | 315/246 |

* cited by examiner

THIN FILM SHEET INCLUDING POWER LINES, LIGHTS, AND SENSORS

CROSS-REFERENCE TO RELATED APPLICATION

This application claims the benefit of U.S. Provisional Application No. 62/405,431 filed Oct. 7, 2016, which is expressly incorporated herein by reference.

TECHNICAL FIELD

The present disclosure relates generally to a thin film sheet that includes power lines, lights, and sensors. More particularly, the present disclosure relates to devices in which both light sources and sensors are both provided on a single substrate.

BACKGROUND

In general, the food industry is faced with a need to increase the ability to monitor the integrity of food during transit. For example, the Food Safety Modernization Act broaden the regulatory authority of the US Food and Drug Administration ("FDA") to oversee transportation of food throughout the United States.

In addition to regulatory concerns, the food industry as well as the medical supplies industry is faced with additional demands to supply data monitoring data to ensure the integrity of food or other perishable good. For example, large retailers may require that a shipper provide proof that a certain load of cargo has maintained precise temperature control throughout a cross-country trip.

However, tractor trailers are not typically equipped to monitor cargo loads. Furthermore, like all vehicles, tractor trailers must conserve energy resources since the electricity in tractor trailers must come from a battery source.

In addition to monitoring needs, tractor trailers also require sufficient lighting within an associated trailer. As with monitoring, the particular needs of the automobile industry demand that lighting conserve energy resources as well. Furthermore, since the total holding capacity of a tractor trailer directly affects the amount of inventory the shipper can transport, compactness and space-considerations must also be considered.

BRIEF DESCRIPTION OF THE DRAWINGS

The accompanying figures where like reference numerals refer to identical or functionally similar elements and which together with the detailed description below are incorporated in and form part of the specification, serve to further illustrate an exemplary embodiment and to explain various principles and advantages in accordance with the present invention. These drawings are not necessarily drawn to scale.

DETAILED DESCRIPTION

The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order (i.e., processes or steps that are not so limited may be performed in any order).

Furthermore, elements having the same number represent the same element across the various figures, and throughout the disclosure. Their description is not always repeated for each embodiment, but may be inferred from previous descriptions. Elements that have the same number but have the addition of a letter designator indicate distinct embodiments of a more generic element.

Overview

Figure 1:
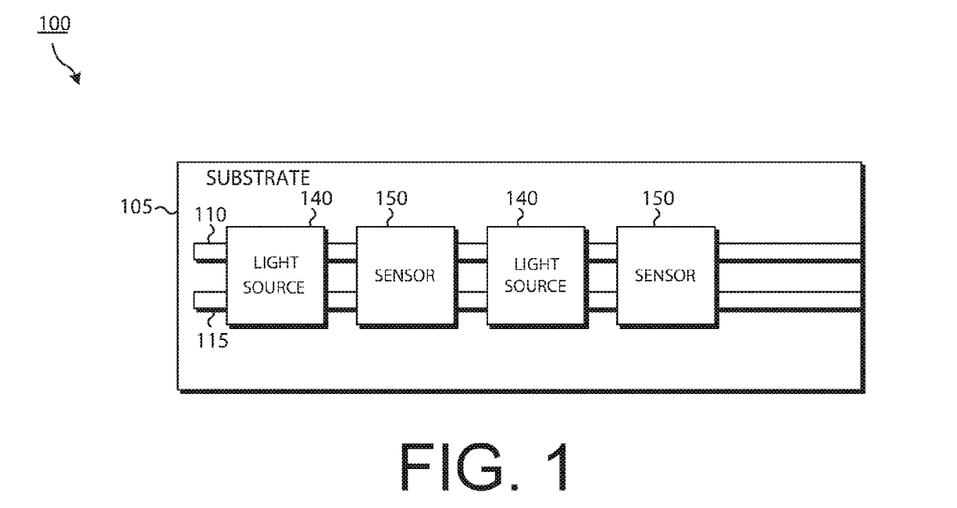
FIG. 1 is a plan view of the thin film sheet having light sources and sensors according to the disclosed embodiments.
Figure 2:
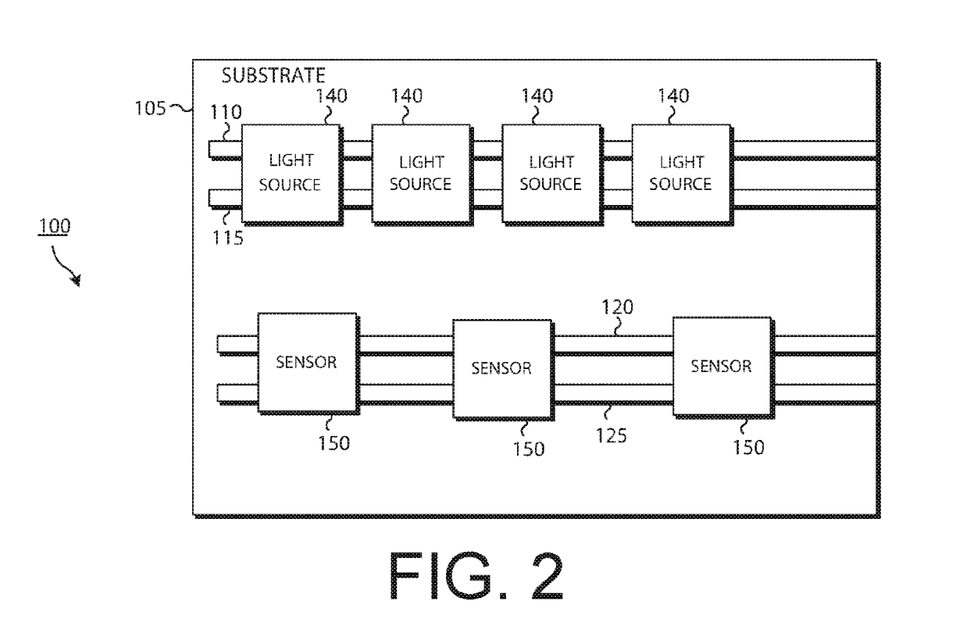
FIG. 2 is a plan view of the thin film sheet having light sources and sensors according to the disclosed embodiments.

In general, the present disclosure relates to a thin film sheet that includes at least two power lines connected to light sources and sensors. FIG. 1 shows a plan view of a thin film sheet with light sources and sensors serially connected to the same power lines. FIG. 2 shows a plan view of a thin film sheet with light sources and light sensors that extend parallel to each other.

FIG. 1 shows a thin film sheet 100 that includes a substrate 105 that includes a pair of electrical connectors as power lines. Specifically, the thin film sheet 100 includes a first electrical connector 110 and a second electrical connector 115. The second electrical connector 115 extends parallel to the first electrical connector 110.

The first electrical connector 110 and the second electrical connector 115 can transport both power and information signals to components attached to the pair of electrical connectors. In other embodiments, the first electrical connector 110 can transport power and the second electrical connector 115 can transport power and information signals.

In addition, the second electrical connector 115 may serve as a failsafe for the first electrical connector 110. With this feature, the thin film sheet 100 ensures that a particular shipping cargo load is properly monitored throughout a trip. Otherwise, a simple short in an electrical connector may jeopardize an entire cargo load, due to strict monitoring requirements.

A plurality of light sources 140 are attached to both of the first electrical connector 110 and the second electrical connector 115. In addition, a plurality of sensors 150 are arranged between at least one pair of the plurality of light sources 140 and are connected to the first electrical connector 110. For example, FIG. 1 shows a repeating pattern of light source 140, sensor 150, light source 140, and sensor 150. However, other repeating patterns and non-repeating arrangements are within the scope of the present disclosure.

In other embodiments, the plurality of light sources 140 and the plurality of sensors 150 run on different pairs of electrical connectors. For example, FIG. 2 shows a thin film sheet 100 that includes a first electrical connector 110, a second electrical connector 115, a third electrical connector 120, and a fourth electrical connector 125. The first pair of electrical connectors includes the first electrical connector 110 and the second electrical connector 115. Whereas, the second pair of electrical connectors include the third electrical connector 120 and the fourth electrical connector 125.

The second pair of electrical connector can also transport any combination of information and power, similar to the first electrical connector 110 and the second electrical connector 115. The second pair of electrical connector extends in parallel to the first pair of electrical connectors within the same thin film sheet 100.

As shown in FIG. 2, each of the plurality of sensors 150 are electrically connected to the third electrical connector 120 and the fourth electrical connector 25. Thus, the plurality of sensors 150 extend in parallel to the plurality of light sources 140.

Types of Sensors

The plurality of sensors 150 can be any sensor known to one skilled in the art, or any combination thereof. For example, the plurality of sensors 150 may include a temperature sensor, a humidity sensor, and/or an infrared sensor ("IR sensor"). In other embodiments, the plurality of sensors 150 may include a volatile organic molecule sensor that detects chemicals released by cargo loads during transportation. The volatile organic molecule sensor can detect the presence, and/or evaluation rate, of a volatile organic molecule.

For example, the volatile organic molecule sensors can detect the amount of ethylene (i.e., ethene) emitted from vegetables during transportation. The particular volatile organic molecule can include any molecule emitted from food or other perishable goods, such as carbon dioxide or methane.

Arrangement of Light Sources and Sensors

As discussed above, the plurality of light sources 140 and the plurality of sensors 150 can be arranged in different arrangements, such as in series on the same pair of electrical connectors (FIG. 1) and on a different pair of electrical connectors (FIG. 2).

In some embodiments, the plurality of light sources 140) and the plurality of sensors 150 are completely covered with an upper substrate or layer. In other embodiments, only the plurality of light sources 140 are covered, and the plurality of sensors 150 remain uncovered (either partially or entirely). Similarly, in other embodiments, both the plurality of light sources 140 and the plurality of sensors 150 are uncovered.

One of the reasons that at least one of the plurality of sensors 150 are uncovered in some embodiments is so that a sensor 150 can be exposed to the outside environment. For example, if the sensor 150 detects a volatile molecule, it may only detect the volatile molecule if a particular surface of the sensor is exposed. On the other hand, if the sensor 150 detects IR light or movement, the sensor may be covered without affecting the efficacy of the sensor.

In addition, some sensors 150 may be exposed so that a sensor 150 may be easily recalibrated and/or replaced, in some embodiments.

Figure 3:
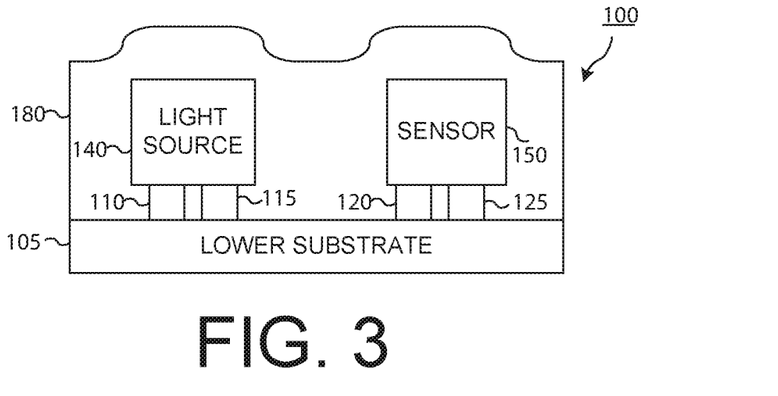
FIG. 3 is a side view of the thin film sheet having covered light sources and sensors according to the disclosed embodiments.
Figure 4:
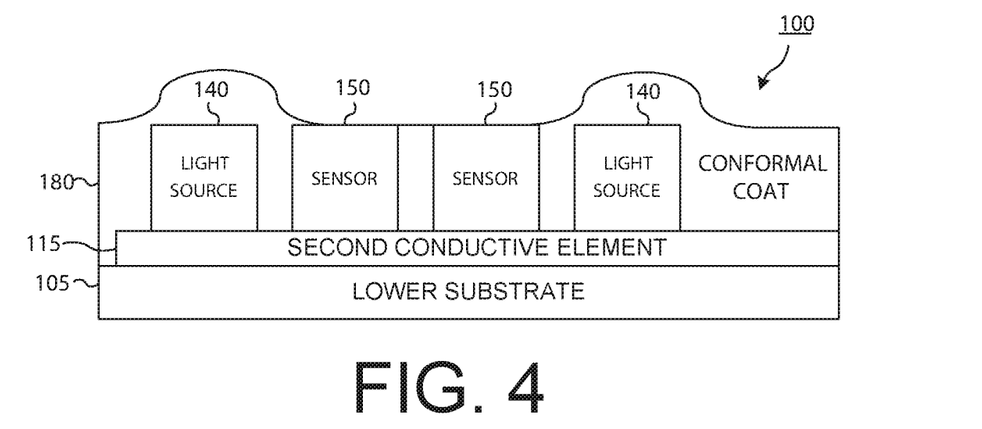
FIG. 4 is a side view of the thin film sheet having covered and uncovered light sources and sensors according to the disclosed embodiments.

FIGS. 3 and 4 show a thin film sheet 100 that includes different combinations of covered and uncovered sensors 150 and light sources 140.

Figure 5:
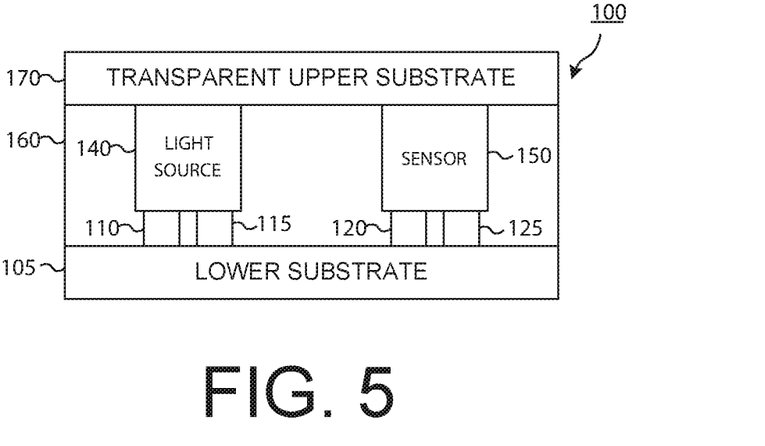
FIG. 5 is a side view of the thin film sheet having covered light sources and sensors according to the disclosed embodiments.

The material that covers the light sources 140 and the sensors 150 is not particularly limited. For example, FIG. 5 shows a transparent upper substrate 170 that covers both the plurality of light sources 140 and the plurality of sensors 150.

Figure 6:
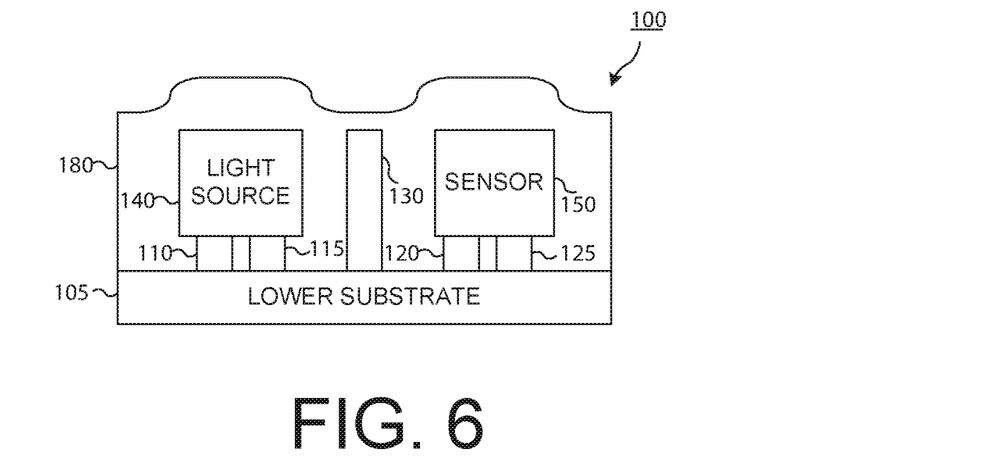
FIG. 6 is a side view of the thin film sheet having a separator between covered light sources and sensors according to the disclosed embodiments.

In addition, some sensors 150 may be overly sensitive to the presence of a light source 140. On the other hand, a light source 140 could be overly sensitive to the presence of a sensor 150, as interference. In order to compensate for these types of sensors 150 and light sources 140, the thin film sheet 100 may include a separator 130 that is spaced between the sensor 150 and the light source 140. FIG. 6 shows a separator 130 that separates a light source 140 from a sensor 150. In other embodiments, the separator 130 may separate light sources 140 from other light sources 140, or separate sensors 150 from other sensors 150.

Thin Film Wire Harness

Figure 7:
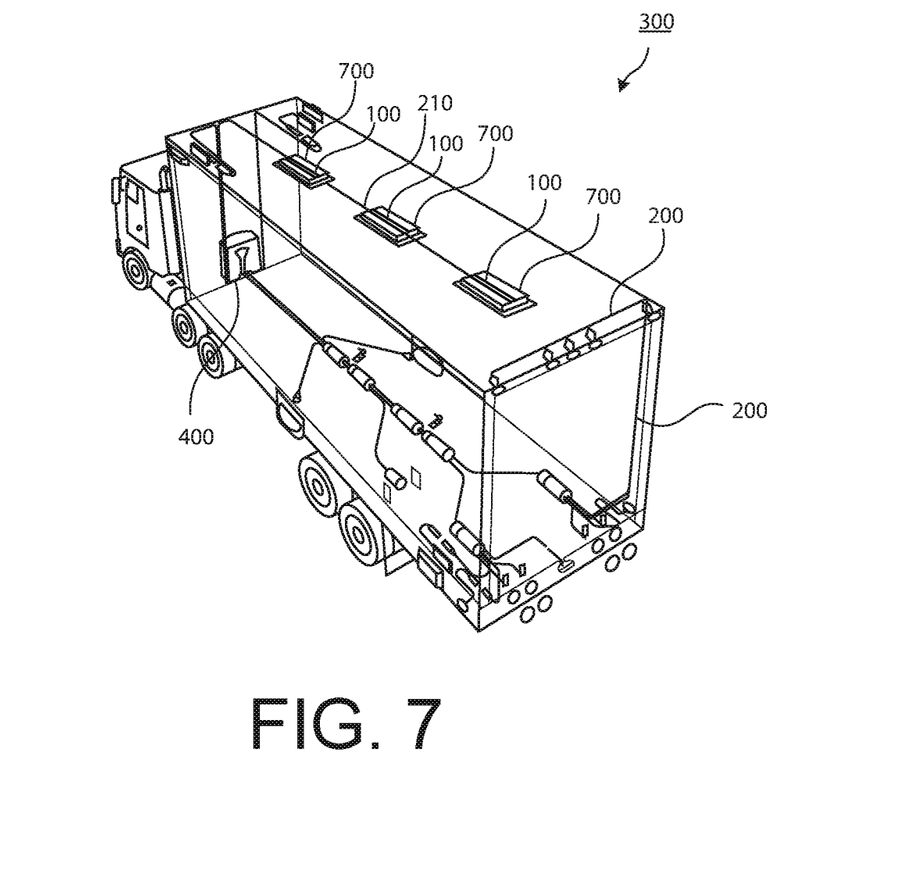
FIG. 7 is a perspective view of a tractor trailer including a nose box, a dome light, and thin film sheets connected together in a wire harness according to the disclosed embodiments.

The thin film sheet 100 can also be attached together to form a wire harness 200 for a tractor trailer. The wire harness 200 extends around the interior of an associated trailer of a tractor trailer. FIG. 7 shows a wire harness assembly 300 that includes one or more wire harness 200 connected along the interior of a trailer. Since the wire harness 200 includes the thin film sheet 100, the wire harness 200 may also include the plurality of light sources 140 and the plurality of sensors 150.

Moreover, the wire harness 200 that includes light sources 140 and sensors 150 spread throughout results in a distributed network of lights and sensors throughout the interior of a trailer. Thus, the integrity of a cargo load (such as food or medical supplies) can be precisely monitored, due to the integrated sensors 150.

Furthermore, the wire harness 200 can be attached to, and spread-out through, a trailer's interior at particular locations in order to maximize monitoring efficacy. Other embodiments may include multiple wire harnesses 200 spread throughout a tractor trailer, such as the internal harness. For example, FIG. 7 shows multiple wire harnesses 200.

In other embodiments, the light plurality of light sources 140 and the plurality of sensors 150 may also be located in other locations, either in addition to or instead of the wire harness 200 itself.

Dome Lighting with Light Sources and Sensors

In some embodiments, the plurality of light sources 140 and the plurality of sensors 150 may be centralized at a particular location within the trailer. For example, the plurality of light sources 140 and the plurality of sensors 150 may be located within a dome light 700. The dome light 700 may be located anywhere throughout the trailer to provide lighting and monitoring.

The particular arrangement of the light sources 140 and the sensors 150 within the dome light is not particularly limited. For example, the plurality of light sources 140 and the plurality of sensors 150 may be arranged in the manner shown in FIGS. 1 and 2. In other words, the light sources 140 and the sensors 150 may be connected to the same pair of electrical connectors. In other embodiments, the light sources 140 and the sensors 150 may be connected to different pairs of electrical connectors.

Within the dome light 700, the pair of electrical connectors form a configuration other than a straight line, such as shown in FIGS. 1 and 2. For example, the electrical connectors may bend and turn in order to fit within the housing of the dome light 700. However, each of the electrical connectors within a pair of electrical connectors may extend respectively parallel to each other, in some embodiments.

Although FIG. 7 shows an embodiment in which one or more of the thin film sheets 100 are within a dome light 700, the present disclosure is not limited to this embodiment. As will be understood by one skilled in the art, the thin film sheets 100 may be included within a wire harness 200 separately without a dome light 700, as discussed above.

Nose Box Integration

As discussed above, the electrical connectors transport power and information signals between the plurality of light sources 140 and the plurality of sensors 150. In some embodiments, the electrical connectors transport the power and information to, and from, a centralized information center attached to the trailer.

Figure 8:
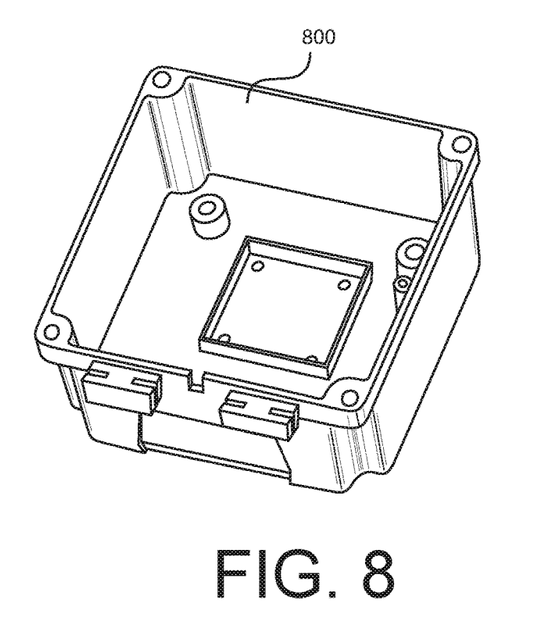
FIG. 8 is a perspective view of the housing of the nose box shown in FIG. 7 according to the disclosed embodiments.
Figure 9:
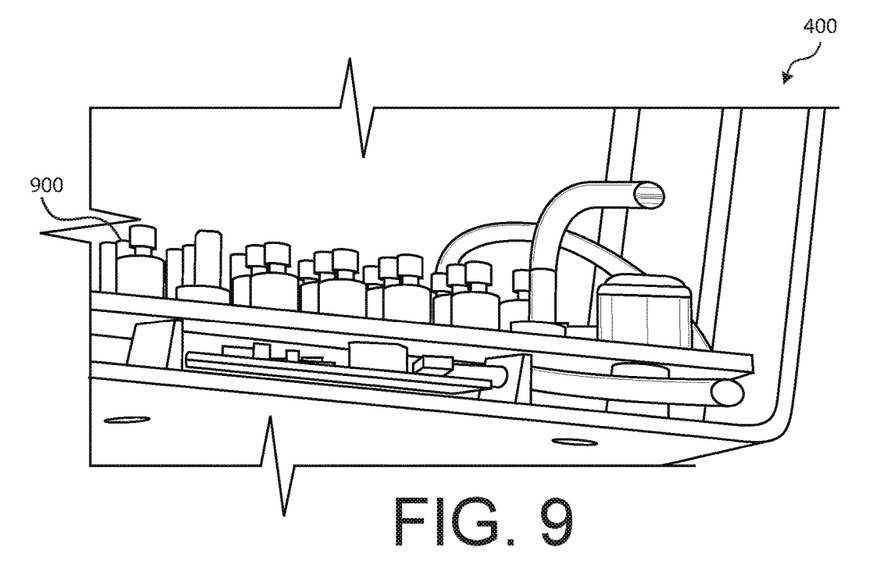
FIG. 9 is a partial perspective view of the interior of the nose box shown in FIG. 7 according to the disclosed embodiments.

For example, FIG. 7 shows a nose box 400 that is modified in some embodiments to accept signals from the sensors 150 and/or to deliver power to the light sources 140 and sensors 150. The nose box 400 is connected to at least one of the multiple harnesses 200. FIG. 8 shows a housing 800 of the nose box 400. FIG. 9 shows a partial view of the circuitry and configuration of the inside of the nose box 400.

Although FIG. 7 shows an embodiment that includes a nose box 400) and a dome light 700 including one or more thin film sheets 100, the present disclosure is not limited to this embodiment. As will be understood by one skilled in the art, the nose box 400 and the thin film sheets 100 may be included in some embodiments without a dome light 700.

Manufacturing Thin Film Sheet

Figure 10:
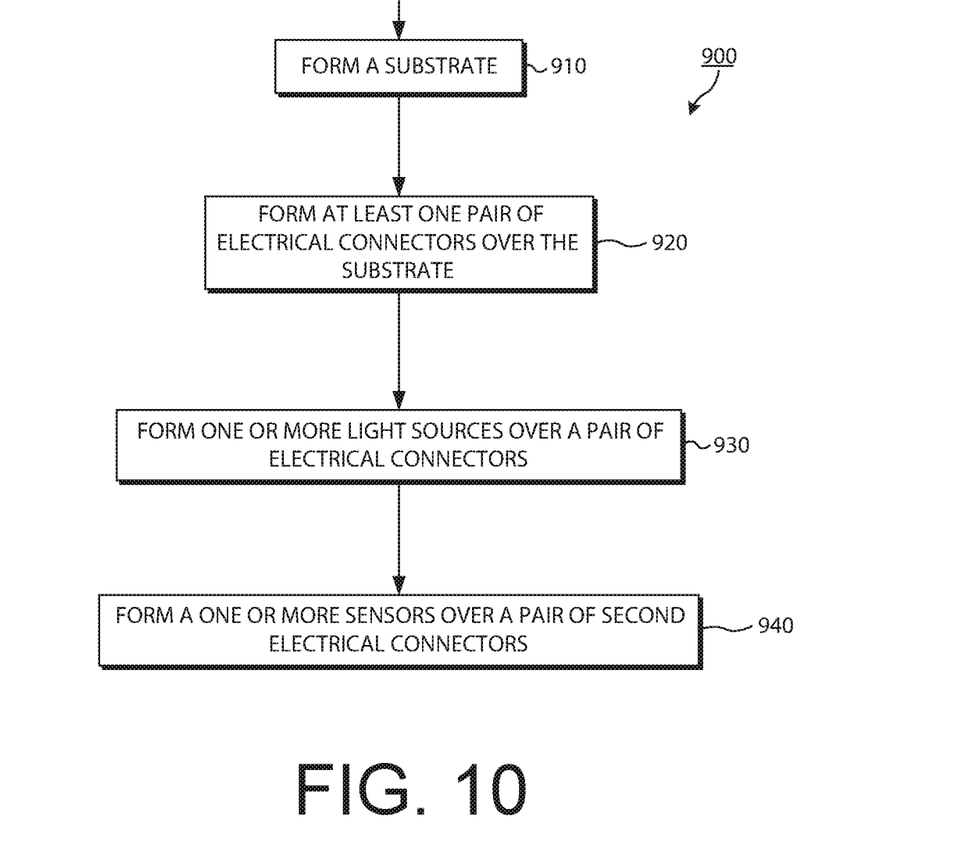
FIG. 10 is a method of manufacturing a thin film sheet according to the disclosed embodiments.

FIG. 10 shows a flow diagram 900 of manufacturing the thin film sheet 100. Note that the order of the steps to manufacturing the film sheet 100 may occur in a different order other than that shown in FIG. 10. For example, FIG. 10 shows a first step 910 of forming a substrate 105. After the substrate 105 is formed, at least one pair of electrical connectors are formed over the substrate 105 in a second step 920. The pair of electrical connectors can include the first electrical connector 110 and the second electrical connector 115 in some embodiments.

After forming at least one pair of electrical connectors, the plurality of light sources 140 and the plurality of sensors 150 are attached to the electrical connectors. For example, FIG. 10 shows the plurality of light sources being connected in a third step 930, and the plurality of sensors being connected in a fourth step 940. However, the light sources 140 and the sensors 150 could be connected in the same step.

CONCLUSION

This disclosure is intended to explain how to fashion and use various embodiments in accordance with the invention rather than to limit the true, intended, and fair scope and spirit thereof. The foregoing description is not intended to be exhaustive or to limit the invention to the precise form disclosed. Modifications or variations are possible in light of the above teachings. The embodiments were chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled. The various circuits described above can be implemented in discrete circuits or integrated circuits, as desired by implementation.

What is claimed is:

1. A lighting and detection system for cargo of a tractor trailer interior, comprising:
    a wiring harness configured to attach to the tractor trailer interior; and
    a dome light electrically couplable to the wiring harness and configured to attach to the tractor trailer interior,
    a nose box electrically couplable to the wiring harness and configured to receive a cargo load sensor signal from at least one of the wiring harness and the dome light, wherein
    at least one of the wiring harness and the dome lighting includes a thin film sheet configured to light and monitor the tractor trailer interior and transmit the cargo load sensor signal to the nose box, the thin film sheet comprises:
    a substrate;
    a first electrical connector attached to the substrate;
    a second electrical connector different from the first electrical connector that is attached to the substrate and that extends substantially parallel to the first electrical connector;
    a plurality of light sources that are each connected directly to the first electrical connector and the second electrical connector, the plurality of light sources extend substantially parallel to the first electrical connector and the second electrical connector on the substrate; and
    a plurality of sensors attached to the substrate.

2. The lighting and detection system according to claim 1, wherein the plurality of sensors are attached to the first electrical connector and the second electrical connector.

3. The lighting and detection system according to claim 2, wherein the plurality of sensors are arranged in between each of the plurality of light sources on the first electrical connector and the second electrical connector.

4. The lighting and detection system according to claim 1, wherein the plurality of sensors are arranged in series with the plurality of light sources along the first electrical connector and the second electrical connector in a repeating pattern.

5. The lighting and detection system according to claim 1, wherein the thin film sheet further comprises:
    a third electrical connector attached to the substrate; and
    a fourth electrical connector that is attached to the substrate and that extends parallel to the third connector, wherein
    the plurality of sensors are electrically connected to the third electrical connector and the fourth electrical connector such that the plurality of sensors extend parallel to the plurality of light sources separately attached to the first electrical connector and the second electrical connector.

6. The lighting and detection system according to claim 5, wherein the third electrical connector and the fourth electrical connector transfer power and information signals.

7. The lighting and detection system according to claim 1, wherein the first electrical connector and the second electrical connector transfer power and information signals.

8. The lighting and detection system according to claim 1, wherein the plurality of sensors are a plurality of temperature sensors.

9. The lighting and detection system according to claim 1, wherein the plurality of sensors are a plurality of humidity sensors.

10. The lighting and detection system according to claim 1, wherein the plurality of sensors are configured to detect a volatile organic molecule.

\* \* \* \* \*